(12) United States Patent
Liaw et al.

(10) Patent No.: US 9,567,597 B2
(45) Date of Patent: Feb. 14, 2017

(54) ULTRASOUND MEDIATED DELIVERY OF SUBSTANCES TO ALGAE

(71) Applicant: University of Hawaii, Honolulu, HI (US)

(72) Inventors: Eric Liaw, Honolulu, HI (US); Chad B. Walton, Honolulu, HI (US); Ralph V. Shohet, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 0 days.

(21) Appl. No.: 14/400,136

(22) PCT Filed: May 11, 2013

(86) PCT No.: PCT/US2013/040681
§ 371 (c)(1),
(2) Date: Nov. 10, 2014

(87) PCT Pub. No.: WO2013/170235
PCT Pub. Date: Nov. 14, 2013

(65) Prior Publication Data
US 2015/0125960 A1    May 7, 2015

Related U.S. Application Data

(60) Provisional application No. 61/646,234, filed on May 11, 2012.

(51) Int. Cl.
| | | |
|---|---|---|
| *C12N 15/82* | (2006.01) |
| *C12M 1/42* | (2006.01) |
| *C12N 13/00* | (2006.01) |
| *C12N 15/87* | (2006.01) |
| *C12M 1/00* | (2006.01) |

(52) U.S. Cl.
CPC .......... *C12N 15/8207* (2013.01); *C12M 35/04* (2013.01); *C12M 45/00* (2013.01); *C12N 13/00* (2013.01); *C12N 15/87* (2013.01)

(58) Field of Classification Search
None
See application file for complete search history.

(56) References Cited

U.S. PATENT DOCUMENTS

| | | |
|---|---|---|
| 2008/0033296 A1 | 2/2008 | Isern |
| 2010/0068772 A1 | 3/2010 | Downey et al. |
| 2011/0086386 A1 | 4/2011 | Czartoski et al. |
| 2011/0306101 A1 | 12/2011 | De Crecy |
| 2012/0107894 A1 | 5/2012 | Skraly |
| 2015/0125960 A1* | 5/2015 | Liaw ............... C12M 45/00 435/471 |

FOREIGN PATENT DOCUMENTS

WO     WO 2013/170235 A1 * 11/2013

OTHER PUBLICATIONS

Azencott et al., "Influence of the Cell Wall on Intracellular Delivery to Algal Cells by Electroporation and Sonication", Ultrasound in Medicine & Biology, Jun. 28, 2007, vol. 33, No. 11, pp. 1805-1817.
International Search Report and Written Opinion mailed Oct. 4, 2013 in Application No. PCT/US2013/040681.
Shao et al., "A codon-optimized luciferase from *Gaussia princeps* facilitates the in vivo monitoring of gene expression in the model alga *Chlamydomonas reinhardtii*", Current Genetics, Apr. 12, 2008, vol. 53, No. 6, pp. 381-388.

* cited by examiner

*Primary Examiner* — Nita M Minnifield
(74) *Attorney, Agent, or Firm* — Knobbe, Martens, Olson & Bear LLP

(57) ABSTRACT

Embodiments provided herein generally relate to methods and materials for ultrasound-mediated introduction of exogenous substances into microorganisms. Some embodiments relate to methods of introducing an exogenous material into a microorganism such as an algae. The methods can include, for example, providing a microorganism (e.g., algae); providing a population of bubbles that comprise one or more nucleic acid molecules and/or one or more polypeptide or one or more protein molecules; contacting the population of bubbles with the algae; applying ultrasound to the bubbles and algae with sufficient energy to cavitate one or more of bubbles comprising the one or more nucleic acid molecules in proximity to the algae; and maintaining the algae and the one or more burst bubbles comprising the one or more nucleic acid molecules in contact for a period of time sufficient to permit entry of at least one nucleic acid molecule into the algae.

23 Claims, 10 Drawing Sheets

UTMD treated Chlamydomonas reinhardtii. A. UTMD with no microbubbles (plasmid DNA only), B. UTMD with microbubbles + plasmid DNA, and C. Light field and GFP merge of UTMD with microbubbles + plasmid DNA. (Mechanical Index 1.7; 10 second exposure; plasmid DNA encoding for GFP).

ULTRASOUND MEDIATED DELIVERY OF SUBSTANCES TO ALGAE

REFERENCE TO RELATED APPLICATIONS

This application is the U.S. National Phase of International Application PCT/US2013/040681, filed May 11, 2013, and claims priority to U.S. Provisional Application No. 61/646,234, filed May 11, 2012. Each of the priority applications is hereby incorporated by reference in its entirety.

STATEMENT REGARDING FEDERALLY SPONSORED R&D

This invention was made with government support under grant no. RR016453 awarded by the National Institutes of Health. The government has certain rights in this invention.

FIELD

This application relates generally to the fields of molecular, cell biology and microbiology. Embodiments provided herein generally relate to ultrasound-mediated introduction of exogenous substances into microorganisms, for example, transformation of microorganisms such as algae. Some embodiments include methods, compositions, devices related to the same.

BACKGROUND

Unicellular algae represent a potentially inexpensive, scalable, $CO_2$-fixing, phototrophic source of biopharmaceuticals, vaccines, antibodies, biofuels, food additives, cosmetics, animal feed additives, pigments, polysaccharides, fatty acids, biomass, and a wide array of various other chemical products. The ability of algae to act as bioreactors for the production of the above-listed substances, has led to considerable efforts to understand the complexities of these microscopic organisms, and to be able to engineer them for a variety of uses.

Algae also have value as feedstocks, for example, for aquaculture. Microalgae feeds for aquaculture ("aquafeeds") are currently produced in small amounts by hundreds of aquaculture operations and some commercial producers. These supply microalgae feeds, for use by bivalve, fish, shrimp and other aquaculture markets. However, costs are high (>$100/kg of dry biomass), production systems small, and global production of such microalgae aquaculture feeds is at most a few hundred tons a year. Low costs are achievable through strain selection and higher productivity by increasing the scale of production from a few hectares and small ponds to several hundred hectares with much larger growth ponds. Additionally, a very large market for aquaculture feeds could be developed for microalgae biomass containing long chain omega-3 fatty acids, to replace fishmeal and oil, but for this production costs must be reduced. Achieving such a low costs will require more efficient production systems, as well as improved strains.

Various methods have been attempted to engineer and transform a number algal strains. For example, current methods include micro-projectile bombardment, particle gun transformation, gene gun transformation, or simply bioballistics. These methods often makes use of DNA-coated heavy-metal (mostly gold) micro-projectiles and allow transformation of almost any type of cell, regardless of the thickness or rigidity of the cell wall, and also allow transformation of organelles. Additional examples of methods are lipid carrier transformation protocols, electroporation, parental mating, and viral based transformation for example with Agrobacterium.

Unfortunately, in many cases the existing methodologies suffer from poor efficiency, have narrow or limited applicability among different types of algae, result in transformants with poor stability, and/or cause harm to many of the targeted algae. Embodiments described herein generally relate to new and improved methods for the introducing exogenous substances into wide variety of algae, for example, with greater efficiency and success, and wider applicability to a variety of algae.

SUMMARY

The methods, systems, kits, compositions and apparatuses described herein each have several aspects, no single one of which is solely responsible for its desirable attributes. Without limiting the scope of this disclosure as expressed by the claims that follow, the more prominent features will now be discussed briefly. After considering this discussion, and particularly after reading the section entitled "Detailed Description," one will understand how the sample features described herein provide for ultrasound mediated delivery of substances to microorganisms such as algae.

Some embodiments relate to methods of introducing an exogenous material into a microorganism such as an algae. The methods can include, for example, providing a microorganism (e.g., algae); providing a population of bubbles that comprise one or more nucleic acid molecules and/or one or more polypeptide or one or more protein molecules; contacting the population of bubbles with the algae; applying ultrasound to the bubbles and algae with sufficient energy to cavitate one or more of bubbles comprising the one or more nucleic acid molecules in proximity to the algae; and maintaining the algae and the one or more burst bubbles comprising the one or more nucleic acid molecules in contact for a period of time sufficient to permit entry of at least one nucleic acid molecule into the algae.

The algae can be, for example, one or more of unicellular, multicellular, photosynthetic, non-photosynthetic, and the like. The algae can be, one or more of a unicellar green algae, a unicellular red algae, a unicellar yellow-green algae, a unicellular brown algae, a unicellular blue-green algae, a unicellular diatom, a unicellular haptophyte, a unicellular dinoflagellate, a unicellular cyanobacterium, or a unicellular eustigmatophyte. The algae can be, for example, eukaryotic or prokaryotic. In some aspects, the algae can be a microalgae.

The algae can be one or more of *Nannochloropsis* sp., *Micromonas* sp., *Tetraselmis* sp., *Chlamydomonas* sp., *Staurosira* sp., *Entomoneis* sp., *Dunaliella* sp., and the like. The *Nannochloropsis* can be, for example, one or more of *N. oceanica*, *N. gaditana*, *N. granulate*, *N. limnetica*, *N. oculata*, *N. salina*, or the like. The *Micromonas* can be, for example, *M. pusilla*. The *Tetraselmis* can be, for example, one or more of *T. alacris*, *T. apiculata*, *T. ascus*, *T. astigmatica*, *T. chuii*, *T. convolutae*, *T. cordiformis*, *T. desikacharyi*, *T. gracilis*, *T. hazeni*, *T. impellucida*, *T. inconspicua*, *T. levis*, *T. maculata*, *T. marina*, *T. micropapillata*, *T. rubens*, *T. striata*, *T. suecica*, *T. tetrabrachia*, *T. tetrathele*, *T. verrucosa*, and *T. wettsteinii*, and the like. The *Chlamydomonas* can be, for example, one or more of *C. reinhardtii*, *C. caudata*, *C. moewusii*, *C. nivalis*, and the like. The *Staurosira* can be, for example, one or more of *S. construens*, *S. elliptica*, *S. venter*, and *S. pinnata*, and the like. The *Ento-*

*moneis* can be, for example, *E. Alata, E. paludosa, E. punctulata, E. pulchra, E. ornate*, and the like. The *Dunaliella* can be, for example, *D. acidophila, D. bardawil, D. bioculata, D. lateralis, D. maritima, D. minuta, D. parva, D. peircei, D. polymorpha, D. primolecta, D. pseudosalina, D. quartolecta, D. salina, D.* sp. 006, *D.* sp. 336, *D.* sp. BSF1, *D.* sp. BSF2, *D.* sp. BSF3, *D.* sp. CCMP 1641, *D.* sp. CCMP 1923, *D.* sp. CCMP 220, *D.* sp. CCMP 367, *D.* sp. FL1, *D.* sp. hd10, *D.* sp. SAG19.6, *D.* sp. SPMO 109-1, *D.* sp. SPMO 112-1, *D.* sp. SPMO 112-2, *D.* sp. SPMO 112-3, *D.* sp. SPMO 112-4, *D.* sp. SPMO 128-2, *D.* sp. SPMO 200-2, *D.* sp. SPMO 200-3, *D.* sp. SPMO 200-8, *D.* sp. SPMO 201-2, *D.* sp. SPMO 201-3, *D.* sp. SPMO 201-4, *D.* sp. SPMO 201-5, *D.* sp. SPMO 201-6, *D.* sp. SPMO 201-8, *D.* sp. SPMO 202-4, *D.* sp. SPMO 207-3, *D.* sp. SPMO 210-3, *D.* sp. SPMO 211-2, *D.* sp. SPMO 300-4, *D.* sp. SPMO 300-5, *D.* sp. SPMO 600-1, *D.* sp. SPMO 601-1, *D.* sp. SPMO 980625-1E, *D.* sp. SPMO 9806254E, *D.* sp. SPMO BP3, *D. tertiolecta, D. viridis*, and the like.

The providing an algae can include providing a population of algae. The population of algae can include one or more of the algae listed above or described herein. The algae can be, for example, present at a concentration of $10^2$-$10^{12}$ cells per 1 mL of culture, $10^5$-$10^{10}$ cells per 1 mL of culture, and the like.

The bubbles can be, for example, microbubbles. The bubbles (including microbubbles) can include, for example, a substance that includes or is one or more of a lipid, a protein, a surfactant, a polyelectrolyte multilayer shell, and a polymer. The substance can be or include, for example, one or more of 1,2-dipalmitoyl-sn-glycero-3-phosphatidylcholine and 1,2-dipalmitoyl-sn-glycero-3-phosphatidylethanolamine, SPAN-10/TWEEN-40, albumin, alginate, poly(D, L-lactide-co-glycolide) (PLGA)), poly(vinyl alcohol) (PVA), and polyperfluorooctyloxycaronyl-poly(lactic acid) (PLA-PFO), and the like. In some embodiments, the bubbles can have diameter of about 0.2 µM-5 µM, a diameter of about 1 µM-3 µM, and the like.

The one or more nucleic acid molecule can be or include, one or more of a miRNA, shRNA, siRNA, circular nucleic acid construct, plasmid DNA, a transposase construct, or a viral nucleic acid construct. The one or more nucleic acid molecule can include or be a sequence encoding a protein, a polypeptide or a peptide. The protein, a polypeptide or a peptide can be or include, for example, an antibody, an antibody fragment, an enzyme, a cytokine, a chemokine, an antigen, a neurotrophin, a hormone, a brain derived neurotrophic factor, a fluorescent protein, an interleukin, a growth factor, a toxin, a signal sequence, a transcription factor, a report molecule, a promoter, or a polypeptide or protein comprising a coding sequence and/or non-coding that is at least partially optimized for algal expression, and the like. The one or more nucleic acid molecules and/or one or more polypeptide and/or protein molecules can be loaded onto or coated onto the bubbles. The one or more nucleic acid molecules and/or one or more polypeptide and/or protein molecules can be bound or attached to the bubbles, for example, via an electrostatic or ionic bond, via conjugation, via a covalent bond, van der Waals forces, and the like. The one or more nucleic acid molecules and/or the one or more polypeptide and/or protein molecules can be present at a concentration ranging from about 1 to 1,000 µg/mL of culture or bubble/microbubble solution. The one or more nucleic acid molecules and/or the one or more polypeptide and/or protein molecules can be coated onto the bubbles at a concentration of 0.5 mg to 5 mg per mL final volume, 1 mg nucleic acid per 1.0 or 1.3 mL final volume (e.g., final microbubble solution volume), and the like, for example. In some embodiments the substance is at a concentration that is sufficient to saturate the bubbles, for example, to maximize loading.

The applying ultrasound to the bubbles and algae can include, for example, applying ultrasound at a center frequency range of about 0.2 KHz to about 3 MHz, a center frequency range of about 0.5 KHz to about 1.3 MHz, and the like. The ultrasound can be applied at a Mechanical Index (MI) of between about 0.1 to 4.0, for example. The ultrasound may be applied as either a continuous wave or an arbitrary wave (over the specified time period), for example. The ultrasound is applied at a power range of between about 0.5 and 200 W power range, for example. The algae and the bubbles can be contacted and/or the application of ultrasound can occur in a containment apparatus, for example, a multi-well plate. The containment apparatus can include, for example, an acoustically, non-reflective material such as a plastic, and can have a size that is close to the size of the transducer so the transducer can fit into the apparatus, but with minimal extra space.

The application of ultrasound can include the use of an ultrasonic transducer brought into sufficient proximity with the algae and bubbles to be able to transmit ultrasound to the same. The application of ultrasound can include contacting an ultrasonic transducer with the algae and bubbles, including submerging or immersing the ultrasonic transducer into a solution of media comprising the algae and bubbles. The transducer can have, for example, a diameter that is between 50% and 99%, preferable greater than 80%, of the diameter of a containment apparatus comprising the algae and the bubbles. The application of ultrasound can include, without being limited thereto, applying ultrasound for between about 5 seconds and 25 seconds.

The methods further can include culturing the algae after application of ultrasound. The culturing can include, for example, a duration of about 6 hours to 5 days. The methods further can include visualizing the transformed cell or organism, for example, with a microscope; using the transformed organism or cell as a seed culture, generating offspring, culturing the algae and isolating a product from the algae.

Some embodiments relate to methods of transforming an algae, that include, for example, contacting microalgae at a concentration of between $1\times10^6$ cells to about $1\times10^8$ cells per 1 mL of a solution with microbubbles that include or are loaded with one or more nucleic acid molecules at a concentration of 1-1000 µg per 1 mL of algal solution; applying ultrasound to the contacted microalgae and microbubbles for a period ranging from about 5 seconds to 20 seconds by at least partially submerging an ultrasound transducer into the solution, wherein the ultrasound has one or more of a frequency of 0.2 KHz to 2.0 MHz, a mechanical index (MI) of 0.1 to 4.0, a power range of 0.5 to 200 W; and wherein the applying of ultrasound is sufficient to break or burst one or more microbubbles such that the one or more nucleic acid molecules can enter into one or more of the microalgae. The microbubbles can include, for example, a material at least partially having a positive charge sufficient to create an electrostatic attraction with the one or more nucleic acid molecules, a material at least partially having a negative charge sufficient to create an electrostatic attraction with the one or more at least positively charged molecules, or a material without a charge sufficient to create an electrostatic attraction. The frequency can be, for example, between 0.5 and 1.1. The ultrasound may be transmitted in arbitrary waves or continuous waves.

Some embodiments relate to systems that include a container that includes algae and nucleic acid coated bubbles and an ultrasound transducer immersed in the container for a period of at least 5 seconds and emitting ultrasound waves for a period of at least 5 seconds, for example.

Still further embodiments relate to containers that include a population of algae having a size of less than 1000 microns, and a population of bubbles that includes, for example, one or more nucleic acid molecules, the bubbles at least partially being made or including one or more lipids.

Some embodiments relate to kits that include, for example, one or more of a microorganism, one or more ingredients for forming microbubbles and a nucleic acid construct. The microorganism can be, for example, an algae. The nucleic acid construct can be or include, one or more of a vector, a plasmid, a nucleic acid backbone with or without control sequence or other nucleic acid molecule with or without a coding sequence. The kit wherein at least a portion of the nucleic acid construct includes at least some sequence that is codon optimized for use with the organism. The kits further may include instructions for performing an ultrasound mediated delivery method or part of such a method. The kits further can include, for example, a transducer or part of a transducer.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the systems, methods, devices, and/or processes described herein will become apparent in the teachings that follow.

BRIEF DESCRIPTION OF THE DRAWINGS

The above-mentioned aspects, as well as other features, aspects, and advantages of the present technology will now be described in connection with various embodiments, with reference to the accompanying drawings. The illustrated embodiments, however, are merely examples and are not intended to be limiting.

DETAILED DESCRIPTION

Figure 1:
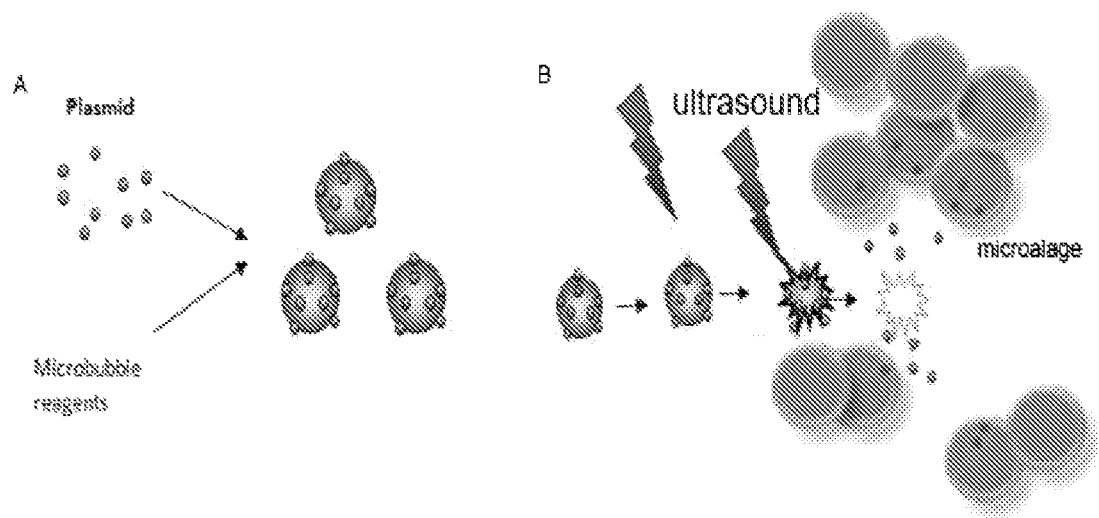
FIG. 1 is a non-limiting overview depiction of an ultrasound targeted microbubble destruction (UTMD) method according to some embodiments.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure. For example, a kit, a system or apparatus may be implemented or a method may be practiced using any number of the aspects set forth herein. In addition, such a kit, system or apparatus may be implemented or such a method may be practiced using other structure, functionality, or structure and functionality in addition to or other than one or more of the aspects set forth herein.

Ultrasound Mediated Delivery of Substances to Microorganisms

Algae represent a class of organisms with many uses, but still with great potential for further understanding, improvement and utilization. The techniques, kits, compositions of matter and apparatuses disclosed herein provide exciting advances in the field of genetic engineering microorganisms, particularly organisms such as algae. The instant technology, in some embodiments facilitates genetic engineering of microorganisms such as algae by facilitating modifications or improvements of algae, for example, to produce recombinant molecules, express markers, localize substances, etc. A whole variety of improvements and new or improved uses of algae are now possible with this technology. For example, this new platform technology can permit rapid modification of algae strains using an ultrasound-mediated method that provides for more efficient modifications cells, manipulation and study of cells, and production of algae engineered to better produce useful substances (e.g., long chain omega-3 fatty acids, carotenoid pigments, proteins, peptides, etc.). The technology can be utilized, for example, to help optimize the biochemical profile of chosen algal strains to satisfy the requirements for aquafeed. The technology has the potential to permit improved engineering of algae, which may lead to replacing fishmeal with microalgae as the primary source of nutrients for aquaculture. Due to the relative inexpensive nature of this approach, with attainable instrumentation costs, academic labs, research institute, biotech companies and larger commercial farms can have on-site UTMD capabilities to enhance their microalgae transformation, selection and propagation activities. The methods described herein according to some embodiments, do not rely on the use of agrobacterium or other virus mediated delivery systems, electroporation, bioballistics, and other previous delivery methods, and can be incorporated into complex bioreactor construction to serve as a seeding mechanism and rapid method for obtaining stable algae strains.

Embodiments provided herein generally are drawn to methods, systems, kits, compositions and apparatuses related to the use of ultrasound to facilitate the delivery of substances into cells and microorganisms. Specifically, some embodiments relate to the use of ultrasound to introduce an exogenous material into algae. The methods can include, among other things, providing an algae and a population of bubbles, which bubbles include one or more materials that are desired to be delivered into the algae, contacting the algae with the bubbles and applying ultrasound to the contacted materials with sufficient energy to destroy the bubble, for example, to cavitate the bubble. Some embodiments, relate specifically to ultrasound targeted destruction of bubbles, for example, microbubbles (UTMD). Upon destruction or cavitation, the exogenous material can enter into an algal cell. The methods are broadly applicable and effective with a variety of algae strains.

FIG. 1 is a non-limiting depiction providing an overview of an ultrasound targeted microbubble destruction (UTMD) method according to some embodiments. In the non-limiting example that is depicted, side A of the diagram includes plasmid DNA and microbubble reagents that are contacted or mixed so that one or more of the plasmid DNA constructs is at least partially attached to the microbubbles. In some embodiments, the plasmid DNA actually can be bound to the microbubbles via an electrostatic attraction between the at least partially cationic microbubble and the generally anionic plasmid DNA. At side B of the depiction the coated microbubbles are in proximity with a population of microalgae. Ultrasound is applied to the coated microbubbles, which results in the destruction of the bubbles, presumably via cavitation (discussed more fully below). The destruction of the microbubbles results in the plasmid DNA being in proximity with the algae and being able to enter one or more of the algae.

Some embodiments relate to kits that include an algae strain that to which it is desired to deliver an exogenous substance or molecule. The kits can include for example, one or of a population of algae, ingredients for a bubble preparation, an already prepared bubble preparation, a nucleic acid construct (with or without a desired insert; and the construct with or without insert can be codon optimized for use in algae), an ultrasound transducer, instructions for practicing one or more of the methods described herein, and the like.

Still some embodiments relate to systems and apparatuses for practicing the methods described herein. Some embodiments relate to compositions and combination products that include, among other things, algae and bubbles comprising or including a substance that is desired for delivery into the algae. Provided herein are methods with parameters for practicing the methods and utilizing the systems, kits and compositions with a variety of algae strains, as described herein. The methods can permit improved transfection and molecule delivery efficiencies.

Microorganisms

The methods, systems, kits, compositions, devices, and the like can be used to facilitate the delivery of a variety substances to microorganisms. The methods, systems, kits, compositions and devices can be applied to many different cells and microorganisms, but will be discussed primarily in connection with algae. Any suitable algae can be transformed or have delivered to it the substances described herein. For example, the algae can be one or more of unicellular, multicellular, eukaryotic, prokaryotic, photosynthetic, and the like. The algae can be a microalgae, for example. The algae can be a unicellular green algae, a unicellular red algae, a unicellular yellow-green algae, a unicellular brown algae, a unicellular blue-green algae, a unicellular diatom, a unicellular haptophyte, a unicellular dinoflagellate, a unicellular cyanobacterium, or a unicellular eustigmatophyte.

The algae can be or include one or more of the following: a *Nannochloropsis* sp., a *Micromonas* sp., a *Tetraselmis* sp., a *Chlamydomonas* sp., a *Staurosira* sp., a *Entomoneis* sp. and a *Dunaliella* sp. The *Nannochloropsis* can be, for example, one or more of *N. oceanica, N. gaditana, N. granulate, N. limnetica, N. oculata, N. salina*, and the like. The *Micromonas* can be, for example, *M. pusilla* or the like. The *Tetraselmis* can be, for example, one or more of *T. alacris, T. apiculata, T. ascus, T astigmatica, T. chuii, T. convolutae, T. cordiformis, T. desikacharyi, T. gracilis, T. hazeni, T impellucida, T. inconspicua, T. levis, T. maculata, T. marina, T. micropapillata, T. rubens, T. striata, T. suecica, T. tetrabrachia, T. tetrathele, T. verrucosa*, or *T. wettsteinii*, and the like. The *Chlamydomonas* can be, for example, one or more of *C. reinhardtii, C. caudata, C. moewusii*, or *C. nivalis*, and the like. The *Staurosira* can be, for example, one or more of *S. construens, S. elliptica, S. venter, S. pinnata*, and the like. The *Entomoneis* can be, for example, one or more of *E. Alata, E. paludosa, E. punctulata, E. pulchra*, or *E. ornate*, and the like. The *Dunaliella* can be, for example, one or more of *D. acidophila, D. bardawil, D. bioculata, D.*

*lateralis, D. maritima, D. minuta, D. parva, D. peircei, D. polymorphs, D. primolecta, D. pseudosalina, D. quartolecta, D. salina, D.* sp. 006, *D.* sp. 336, *D.* sp. BSF1, D. sp. BSF2, *D.* sp. BSF3, *D.* sp. CCMP 1641, *D.* sp. CCMP 1923, *D.* sp. CCMP 220, *D.* sp. CCMP 367, *D.* sp. FL1, *D.* sp. hd10, *D.* sp. SAG19.6, *D.* sp. SPMO 109-1, *D.* sp. SPMO 112-1, *D.* sp. SPMO 112-2, *D.* sp. SPMO 112-3, *D.* sp. SPMO 112-4, *D.* sp. SPMO 128-2, *D.* sp. SPMO 200-2, *D.* sp. SPMO 200-3, *D.* sp. SPMO 200-8, *D.* sp. SPMO 201-2, *D.* sp. SPMO 201-3, *D.* sp. SPMO 201-4, *D.* sp. SPMO 201-5, *D.* sp. SPMO 201-6, *D.* sp. SPMO 201-8, D. sp. SPMO 202-4, *D.* sp. SPMO 207-3, *D.* sp. SPMO 210-3, *D.* sp. SPMO 211-2, *D.* sp. SPMO 300-4, *D.* sp. SPMO 300-5, *D.* sp. SPMO 600-1, *D.* sp. SPMO 601-1, *D.* sp. SPMO 980625-1E, *D.* sp. SPMO 9806254E, *D.* sp. SPMO BP3, *D. tertiolecta, or D. viridis,* and the like.

The algae can be part of a population of algae that is homogenous or heterogeneous between species, genre and/or strains. Any suitable concentration of algae can be utilized. For example, the concentration can be $10^2$-$10^{15}$ cells per 1 mL of culture or 1 mL of bubbles. In some embodiments, the concentration can be between about $10^5$-$10^{10}$ cells per 1 mL of culture and/or bubble preparation.

Bubbles

In some embodiments, the bubbles can include or be made of any suitable material for use in the methods described herein. For example, the bubbles (e.g., the bubble shell or membrane) can include or be made of a lipid material, a protein material such as albumin, a surfactant, a polymer or a polyelectrolyte multilayer shell. In some embodiments, the bubbles can be made of a substance to which the material that is to be delivered can attach or be bound. As noted, the bubbles can have an electrostatic charge that can facilitate electrostatic attachment of a substance with an opposite charge (e.g., negatively charged DNA binding to a positively charged lipid, or a negatively charged shell binding to a positively charged substance). In some embodiments, the substance that is to be delivered can be covalently bound to the bubbles via any suitable covalent bond or chemical group. Also, preferably the bubbles are formed such that upon application of ultrasound, the bubbles will cavitate, burst, collapse, etc. in order that the substance for delivery can enter into a cell.

Examples of non-limiting lipids that can be used alone or in combination with another lipid or another substance, include 1,2-dipalmitoyl-sn-glycero-3-phosphatidylcholine, 1,2-dipalmitoyl-sn-glycero-3-phosphatidylethanolamine, and the like. Examples of surfactant shells include, but are not limited to SPAN-10/TWEEN-40, and the like. Examples of polymers include, but are not limited to, alginate, poly (D,L-lactide-co-glycolide) (PLGA)), poly(vinyl alcohol) (PVA), polyperfluorooctyloxycaronyl-poly(lactic acid) (PLA-PFO). Examples of protein shells include, but are not limited to, albumin. Examples of multilayer shells include, but are not limited to, polyelectrolyte multilayers. The bubbles can be filled, for example, with a gas and/or fluid, such as but not limited to, air, nitrogen or perfluorocarbon.

The bubbles can be of any suitable size for carrying or transporting the substance. Preferably, the bubbles can be microbubbles. In some embodiments, the microbubbles can have a size (e.g., diameter) of between about 0.2 μM-5 μM. In some embodiments the microbubbles can have a size of about 1 μM-3 μM.

Delivery Substance

The methods, compositions, systems, kits and apparatuses can be used to deliver a wide variety of substances to a cell of interest using ultrasound. In general, the substance that is to be delivered can be loaded into, onto or attached or at least partially bound to a bubble. As noted that attachment can be accomplished via any suitable mechanism such as for example, an electrostatic attraction or an ionic bond, a covalent bond, hydrogen bonding, van der Waals forces, conjugation, and the like. Non-bound substance can be washed away or otherwise removed or can be left in the solution if desired.

In some embodiments, cells can be transformed by delivery of nucleic molecules. Examples of nucleic acid molecules include without limitation DNA, RNA, linear DNA, circular DNA, cDNA, miRNA, shRNA, siRNA, as well as constructs of any of the same such as vectors, plasmids, viral constructs (e.g., CMV, AAV, CaMV, SV40, lentivirus, retrovirus), and the like. The nucleic acid molecule can be or include a plasmid, a transposase construct, a viral nucleic acid construct, a nucleic acid encoding a protein, a polypeptide, amino acid, or a peptide including any of those described below and elsewhere herein. The nucleic acid molecule can be codon optimized for a given organism or cell, for example, algae or a particular family or strain of algae. The optimization can be done per any suitable protocol.

In some embodiments, peptides, polypeptide amino acid or a protein can be delivered. Examples of such substances include, without limitation, an antibody, an antibody fragment, an enzyme, a cytokine, a chemokine, an antigen, a neurotrophin, a hormone, a brain derived neurotrophic factor, a fluorescent protein, an interleukin, a growth factor, a toxin, a signal sequence, a transcription factor, a report molecule, a promoter, a polypeptide or protein whose coding sequence is optimized for algal expression. The peptide, polypeptide or protein can be loaded into or onto the bubble and then delivered as described herein (e.g., destroying the bubble in proximity to the target cell such that the substance can contact and enter the target).

Non-limiting examples of substances that can be delivered directly or via a coding nucleic acid molecule include: Cytokines: Adiponectin, Angiopoietin, Apoliprotein, B type Natriuretic Peptide, B-Cell Activating Factor, Beta Defensin, Betacellulin, Bone Morphogenetic Protein, EBI3, Endoglin, Flt3 Ligand, Follistatin, Hedgehog Protein, Interferon, Interleukin, Leukemia Inhibitory Factor, Resistin, Serum Amyloid A, Thrombopoietin, Trefoil Factor, Tumor Necrosis Factor, Visfatin, and the like; Growth Factors: Activin, Colony Stimulating Factor, CTGF, Epidermal Growth Factor, Erythropoietin, Fibroblast Growth Factor, Galectin, Growth Hormone, Hepatocyte Growth Factor, IGFBP, Insulin, Insulin-Like Growth Factor, Keratinocyte Growth Factor Leptin Macrophage Migration Inhibitory Factor, Melanoma Inhibitory Activity, Myostatin, Noggin, Omentin, Oncostatin-M, Osteoprotegerin, PDGF, Placental Lactogen, Prolactin, RANK Ligand, Retinol Binding Protein, Stem Cell Factor, Transforming Growth Factor, VEGF, and the like; Chemokines: BRAK (CXCL14), ENA 78, Eotaxin, Fractalkine, GRO, HCC-1, Interleukin-8 (CXCL8), IP-10 (CXCL10), I-TAC (CXCL11), Lymphotactin (XCL1), MCP, MDC (CCL22), MEC (CCL28), MIG (CXCL9), MIP, NAP-2 (CXCL7), Platelet Factor-4 (CXCL4), Rantes (CCL5), SDF (CXCL12), TARC (CCL17), and the like; CD Antigens; Neurotrophins: Beta-Nerve Growth Factor, Ciliary-Neurotrophic Factor, Glia Maturation Factor, Pigment Epithelium-Derived Factor, and the like; Hormones: Endothelin, Exendin, FSH, GHRP, GLP, Glucagon, HCG, Inhibin A, LHRH, Peptide Hormones, PTH, Stanniocalcin, Thymosin, Thyrostimulin, TSH, and the like; Enzymes: 14-3-3, Activating Transcription Factor, Adenylate Kinase, Aldolase, Aurora Kinase, Calcium and Integrin Binding, Carbonic Anhydrase, Casein Kinase-2, Creatin Kinases, Cyclin, Cyclin-Dependent Kinase, Cyclophilin, Deaminase, Decarboxylase, Dehydrogenase, DNA Polymerase, EGF Receptor, Endonuclease, Enolase, Enteropeptidase/Enterokinase, Epimerase, Esterase, FGF Receptors, FK506 Binding Protein, Gluteradoxin, Glycosylase, Hexokinase, Hydratase, Hydrolase, Hydroxylase, Isomerase, Jun N-terminal Kinase, Jun Proto-Oncogene, Kallikrein, Ligase, Lipase, Lyase, LYVE1, Matrix Metalloproteinase, Mitogen-Activated Protein Kinase, Mutase, Natural Enzymes, Nuclease, Nucleotidase, Nudix Type Motif, Oxidase, Oxygenase, Paraoxonase, Peptidase, Peroxiredoxin, Peroxisome Proliferator Activated Receptor, Phosphatase, Phosphoinositide 3-kinase, Phosphorylase, Polymerase, Proteasome, Protein Kinase Akt1/PKB alpha, Protein Kinase-A, Protein Kinase-C, Protein Kinases, Reductase, Secreted Phospholipase A2, Synthase, Synthetase, TIE1, TIE2, Transferase, Tyrosine Kinase, Ubiquitin Conjugating Enzyme, VEGF Receptors, and the like; Viral Antigens: Borrelia, Chagas, Chikungunya, Chlamydia, Cytomegalo, Dengue, EBV, Encephalitis, Hantavirus, HBsAg, Hepatitis A, Hepatitis B, Hepatitis C, Hepatitis D, Hepatitis E, Herpes, HIV, HTLV, Influenza, Malaria, Measles, Mycoplasma, Papillomavirus, Parvovirus, Rubella, SARS, Toxoplasma, Treponema, Varicella, West Nile, and the like; Recombinant Proteins: ADP-Ribosylation Factor, Albumin, Annexin, Assembly Protein Complex, Autophagy Related, B Cell Lymphoma, Baculoviral IAP Repeat-Containing, Beta 2 Microglobulin, BID, Calbindin, Calcium Binding Protein, Calmodulin, Cardiac Troponin, Cell Division Cycle, Centrin, Centromere Protein, Charged Multivesicular Body Protein, Chloride Intracellular Channel, Chromatin Modifying Protein, Chromobox, Chromogranin, Chromosome Open Reading Frame, Coagulation Factors, Collagen, Complement Component, C-Reactive Protein, Crystallin, Cystatin, Cytochrome, Cytokeratin, Dickkopf-Related Protein, DNA-Damage Protein, Dynein Light Chain, Endoplasmic Reticulum Protein, Ephrin, Eukaryotic Translation Initiation Factor, Exosome Component, FABP, Ferritin, GABA(A) Receptor-Associated Protein, General Transcription Factor, Guanine Nucleotide Binding Protein, Heat Shock Protein, Hemoglobin, High-Mobility Group, Homer Homolog, Hypoxia-Inducible Factor, Killer Cell, LIN Protein, Melanoma Antigen Family A, Member RAS Oncogene Family, Microtubule-Associated Protein, Myelin Oligodendrocyte Glycoprotein, Myoglobin, Myosin Light Chain, NANOG, Non-Metastatic Cells, Nucleobindin, Outer Membrane Protein, p53, PCNA, POU Class, Prefoldin, Profilin, Programmed Cell Death, Protein-A, A/G & G, Ras-Related C3 Botulinum Toxin Substrate, Regenerating Islet-Derived, Regulator of Calcineurin, Regulator of G-Protein Signaling, Reticulocalbin, Retinoblastoma, Ribosomal Protein, Secretagogin, Selectin, Septin, Serpin, SH3 Domain, Sirtuin, SMAD, Small Nuclear Ribonucleoprotein Polypeptide, SRY (Sex Determining Region Y)-Box, Stathmin, Streptavidin, Superoxide Dismutase, Synaptobrevin, Synaptosomal Associated Protein, Syndecan, Syntaxin, Synuclein, Thioredoxin, TNF receptor-Associated Factor, Trafficking Protein Particle Complex, Transcription Elongation Factor, Transgelin, Tropomyosin, TROVE Domain Family, Trypsin, Tubulin Folding Cofactor, U6 Small Nuclear RNA, Ubiquitin, Vacuolar Protein Sorting, Vimentin, Visinin-Like Protein, and the like; Natural Proteins: Albumin, AntiCoagulation Factors, Aprotinin, Avidin, Coagulation Factors, Fibronectin, Thrombin, Transferrin, and the like; Monoclonal Antibodies: Anti Human Chemokine, Anti Human Cytokine, Anti Human Enzyme, Anti Human Heat Shock Protein, Anti Human Lymphocyte, Anti Mouse Cytokine, Anti Mouse Lymphocyte, Anti Viral, Anti-GST, and the like; Polyclonal Antibodies: Anti-Viral, Anti-GST, and the like; GFP, CFP, YFP, and the like.

Other substances can be delivered as well. Non-limiting examples include lipids, fatty acids, therapeutic compounds (e.g., small molecules, biologics), and active compounds or molecules.

Further embodiments can include, for example, the addition of a signaling or targeting sequence on the material that is to be delivered, for example, the construct (can encode a signaling or targeting sequence)/exogenous material (e.g., polypeptide can include a signaling or targeting sequence). Some examples of such sequences are referenced and incorporated elsewhere herein.

The delivery substance can be present in any suitable amount or concentration. For example, the substance (e.g., nucleic acid molecule, protein, peptide, or polypeptide) may be present at a concentration ranging from about 1 to 10,000 µg/mL of culture or bubble (e.g., microbubble) solution volume, or any range, sub range, or value there between. In some embodiments, the substance (e.g., nucleic acid molecule) can be coated onto the bubbles at a concentration of 1 µg to 4 mg per 1 mL final volume (e.g., microbubble volume) or any value or sub range there between. In some aspects, the substance (e.g., nucleic acid) can be present at a concentration of 1 mg nucleic acid per 1 mL final volume or any value or sub range there between.

Ultrasound Targeted Bubble Destruction

The bubbles can be destroyed using ultrasound as described herein. One example for illustration purposes is ultrasound targeted microbubble destruction (UTMD). It is a technique for transformation of a microorganism or cell in which a substance such as a bioactive molecules, e.g., negatively charged plasmid DNA vectors encoding a gene of interest, are added to the cationic shells of lipid microbubble contrast agents. See FIG. 1A of Walton et al. ("Introduction to the ultrasound targeted microbubble destruction technique," Journal of visualized experiments: JoVE 52 (2011), which is incorporated herein by reference in its entirety, including without limitation for its methods, materials, devices and techniques). In vivo these vector-carrying microbubbles can be administered intravenously or directly to the left ventricle of the heart. In vitro, the microbubbles can simply be added to the media containing the cells of interest. The DNA delivery to the target cell occurs by acoustic cavitation at a resonant frequency of the microbubbles (See id. at FIG. 1B). Without being limited to any particular theory or mechanism of action, it seems likely that the mechanical energy generated by the microbubble destruction results in transient pore formation in the cells. As a result of this sonoporation effect, the transfection efficiency into and across the cells is enhanced.

Ultrasonic Modulation

Any suitable ultrasound instrument may be used with the methods, systems, kits, compositions and devices described herein. Some embodiments relate to the use of a custom ultrasound instrument capable of complete control of all ultrasonic parameters needed to achieve thorough optimization of the ultrasonic parameters for each of the proposed strains. For example, such an instrument can be configured to detect the efficiency of the cavitation in real-time with use of an attached hydrophone. The device further can be configured to modulate frequency, and mechanical index (MI), for example. In terms of varying the center frequency, a range of 0.2 kHz to 3.0 MHz can be utilized or controlled, or more specifically, 0.5 kHz and 1.1 MHz, or any sub range or value there between. A frequency within such a range can effectively resonate the microbubbles. Mechanical index is essentially an overall estimate of power that a given set of ultrasound parameters will transmit. A higher MI is likely to produce a larger bio-effect. In some embodiments, MI can be varied from a benign measure of 0.1 to a maximal energy of 5.0, alternatively 1.1 to 4.0, or any sub range or value there between. In addition to modulation of ultrasonic parameters, DNA concentration from 10-10,000 μg/ml per 1 mL culture (or any sub range or value there between), as well as algal cell density of the reactions from $10^3$ to $10^{13}$ cells per 1 mL culture, $10^5$ to $10^{10}$ cells per 1 mL culture, or any sub range or sub value there between.

The devices can be operated or configured to operate with a power range of between about 0.5 and 200 W power range, or any sub range or sub value there between.

Some embodiments described herein utilize a continuous waveform of unfocused ultrasound. For example, continuous wave blasts through the bubble/algae solution and transform the algae (or delivery non-nucleic acid molecules such as peptides to the algae). The algae can be physically constrained to ensure optimal efficiency in some embodiments, for example, by using a vessel and/or transducer that prevent "escape" or migration of the algae away from out of the optimal location for being contacted with the ultrasonic waves. As one approach, a transducer that is close to the same size as the vessel containing the algae/bubble solution can be immersed into the vessel. Due to having roughly the same size (e.g., diameter or planar width/length), the transducer combined with the borders of the vessel can act to constrain the algae and bubbles.

It should be understood that an arbitrary waveform can be used as well. For example, a wave pulse can be generated and can allow for on/off cycling (i.e., duty cycle). As such the algae can move directly into the path of the waveform generated (refill principle). Otherwise, in some embodiments, some or all of the cavitation might occur at the place where the algae meet the waveform and could be therefore be less efficient. In some embodiments, additional bubbles can be added and the timing of the pulsing can be modified to account for this different approach in some embodiments.

In some aspects the methods can be performed by contacting the loaded bubbles with the organism (e.g., algae) in a container or containment vessel. For example, the container can be a multi well plate (12, 24, 48, 96, etc.). The ultrasonic transducer can be brought into sufficient proximity with the algae and bubbles to be able to transmit ultrasound to them. For example, the transducer can be contacted with the algae and bubbles or a solution holding those. In some embodiments the ultrasonic transducer can be submerged or immersed into the algae/bubbles or a solution of media comprising the algae and bubbles, for example, it can be immersed from 0.1 cm to 10 cm into the solution. In some aspects the transducer can have a diameter that is between 50% and 99% (or any sub range or value there between of the diameter (or width/length of the cross-sectional orthogonal plane) of a containment apparatus comprising the algae and the bubbles. In some aspects the transducer can have a cross sectional area that is between 50% and 99% (or any sub range or value there between of the cross section area (e.g., the cross-sectional area of the orthogonal plane) of the containment apparatus comprising the algae and the bubbles. In some non-limiting embodiments, the ultrasound can be applied for between 1 second and 30 seconds or any sub range or value there between.

Microbubble Cavitation

Ultrasound targeted bubble destruction (e.g., UTMD) can induce a number of biophysical effects, including; cavitation (microbubble collapse), radiant pressure (force created by the ultrasound waves), and microstreaming (sheer forces created by oscillating microbubbles). The primary effect from UTMD is mediated by cavitation. Cavitation can be further defined as the growth, oscillation and collapse of microbubbles with the application of an acoustic field. Microbubble cavitation results in mechanical induction of transient pores up to 100 nm in size and a few seconds half-life. Cavitation can also be divided into stable and inertial categories. Stable cavitation occurs when the microbubbles oscillate stably in a low intensity acoustic field, generating sheer force and microstreaming. Inertial cavitation occurs within a high intensity acoustic field when the microbubbles rapidly expand and then collapse, producing a shock wave and microenvironments of extreme pressure and temperature. Cavitation occurs all of the time during infusion of contrast bubbles to enhance edge detection during cardiac ultrasound. Despite the violence of this phenomenon on a molecular level, there is no evidence of significant damage at a cellular level in the heart at the energies used in conventional diagnostic ultrasound.

UTMD Pulse Duration.

Varying the length of time that the cavitation frequency is applied will result in a relatively higher amount of cavitation, increasing overall efficiency of transfection per UTMD experiment. In some embodiments, the pulse duration can be varied using a typical mechanical index of, for example, 1.3 from 1 second, 60 s, 5 minutes, and 20 minutes.

Cavitation Frequency:

Inertial cavitation is the process wherein a void or bubble in a liquid rapidly collapses, producing a shock wave. Microscopic gas bubbles that are generally present in a liquid will be forced to oscillate due to an applied acoustic field. If the acoustic intensity is sufficiently high, the bubbles will first grow in size and then rapidly collapse. The effect of different transducer frequencies on UTMD efficiency using different frequencies (0.2, 0.5, 1, 1.1, and 3 MHz) can be assessed. Those are common frequencies used in microbubble cavitation experiments done by the inventors. The microbubble preparations used in some of the UTMD experiments described herein range from 3-6 μm with 90-95% at the 5 μm size (determined using Coulter counter analysis; not shown). In some aspects, the higher frequencies can work, but in some cases may be less efficient at generating the inertial cavitation for some of the microbubble sizes specifically listed herein for some embodiments. The frequencies can be generated by any suitable ultrasound apparatus, including for example, one using unfocused transducers.

Acoustic Power/Mechanical Index:

Mechanical index can be used as an overall estimate of sonographic power that a given set of ultrasound parameters will convey. A higher mechanical index can produce a larger bio-effect. The mechanical index has been described herein. In some embodiments it was varied from 0.1 to 4.0. This range was chosen for some embodiments based on the low end typically not producing any inertial cavitation, and the higher end surpassing thresholds for the bubbles used.

Downstream Processing of "Treated" Organism

The organism or cell that has had a substance delivered to it or "treated" can undergo further downstream processing or analysis. For example, the methods can further include culturing, sub culturing, visualizing, imaging, utilizing as a seed culture, propagated, further treated or transformed, purified, and/or have one or more products purified or removed from it.

Targeted Delivery to Cellular Locations or Organelles

Some embodiments herein relate to ultrasound mediated delivery of substances to algae while targeted certain locations, structures, organelles, etc. of the algae. In some embodiments, the nucleic acid sequence that is delivered can include a subsequence that encodes generally (but not always) short amino acid sequences that facilitate the targeting or delivery of desired substances to a particularly location, structure and/or organelle of the algae. For ease of reference, such targeting amino acid sequences will be referred to herein as signal sequences. In other embodiments where a peptide or protein is delivered, the peptide or protein can include a signal sequence that facilitates delivery or arrival of the molecule to a particular location, structure and/or organelle.

Figure 2:
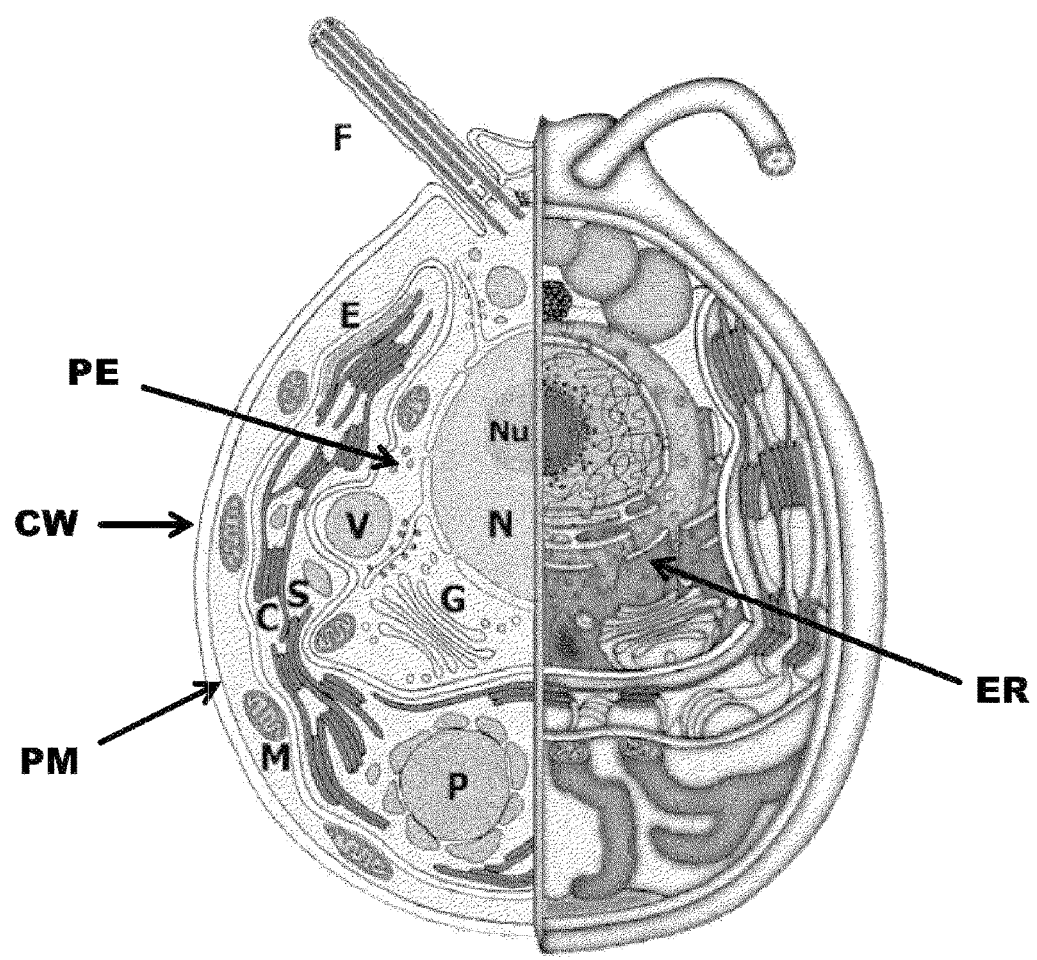
FIG. 2: An artist's rendition of a cross section of a typical wild type *Chlamydomonas reinhardtii* cell. The organelles shown are the flagella (F), the eyespot (E), a vacuole (V), the Golgi body (G), the nucleus (N) which contains the nucleolus (Nu), a chloroplast (C), starch grains (S), the pyrenoid (P), mitochondria (M), the plasma membrane (PM), the cell wall (CW), the endoplasmic reticulum (ER) and smaller organelles such as peroxisomes (PE). Note the large size of the single "U" shaped chloroplast, which is characteristic of the *C. reinhardtii* species.

FIG. 2 is an artist's rendition of a cross sectional view of one example of an algae, C. reinhardtii, that can be utilized in the methods, systems, kits, compositions and devices described herein. The organelles shown are the flagella (F), the eyespot (E), a vacuole (V), the Golgi body (G), the nucleus (N) which contains the nucleolus (Nu), a chloroplast (C), starch grains (S), the pyrenoid (P), mitochondria (M), the plasma membrane (PM), the cell wall (CW), the endoplasmic reticulum (ER) and smaller organelles such as peroxisomes (PE). Note the large size of the single "U" shaped chloroplast, which is characteristic of the *C. reinhardtii* species.

The development of powerful fluorescent microscopes has provided a means to observe the structures and components of various cells with a great amount of detail. Equally important advances have been made in the production and use of fluorescent protein tagging technologies. Fluorescent proteins can be localized to specific regions within the cell using signal sequences, as described in Nelson et al. ("A multicolored set of in vivo organelle markers for co-localization studies in *Arabidopsis* and other plants," *The Plant journal for cell and molecular biology*, 51(6):1126-1136 (2007), which is incorporated herein by reference in its entirety, including all targeting sequences and nucleic acid constructs and sequences, methods and techniques described therein). Therefore, these fluorescent proteins can be targeted to a specific cell organelle and, when used in conjunction with fluorescent microscopy, a live analysis of the cellular dynamics can be observed. Organelle tagging technologies may also aid in the determination of the relationship between mutant or drug-mediated phenotypes and the related cell structure and function. Thus, some embodiments relate to the use of ultrasound mediated delivery of exogenous substances to facilitate the targeted delivery of the exogenous substances to specific organelles or regions of algae.

Although fluorescent injections and the use of fluorescent antibodies have been used in larger eukaryotic cells, genetic transformations using DNA containing a targeted fluorescent protein gene is the only realistic method currently available for fluorescent tagging in algal cells. Green Fluorescent Protein (GFP), a natural protein first isolated from the jellyfish *Aequorea victoria*, is commonly used for fluorescent tagging in modern laboratories. GFP is a desirable marker because it can function in living organisms, is visible with only a LTV light, can be viewed in real time under a fluorescent microscope and can function in a multitude of cell types and species. The GFP protein is small (28 kDa) and can freely enter a cell's nucleus, fill the cytoplasm of a cell or diffuse into cellular organelles.

Organelle markers from Nelson et al. were utilized for delivery to the endoplasmic reticulum, the Golgi body, tonoplasts, peroxisomes, mitochondria, plastids and the plasma membrane. See Nelson et al., which is incorporated herein by reference in its entirety. Cells were genetically transformed using UTMD and were imaged using fluorescent microscopy. Experiments targeting GFP and Cyan Fluorescent Protein (CFN) to algae and to specific algal organelles and locations are described below.

Systems, Apparatuses and Kits

Further embodiments relate to various systems, kits, containers and apparatuses. Some embodiments relate to systems that include for example a container that comprises a microorganism such as an algae and a nucleic acid coated bubbles (e.g., microbubbles), and an ultrasound transducer immersed in the container for a period of time, for example, at least 1 second to 60 seconds, and emitting ultrasound waves for a period of at least 1 second to 30 seconds. Preferably immersing the transducer for at least 2-30 seconds. Preferably emitting ultrasound for 3-15 seconds.

Some embodiments relate to a container comprising a population of algae, for example, one having a size of less than 1000 microns, and a population of bubbles comprising one or more nucleic acid molecules, the bubbles at least partially comprising one or more lipids. The bubbles can be any bubble as set forth herein and can have a substance to be delivered loaded there on, including any substance described herein.

Finally, some embodiments relate to kits that include for example, one or more of a microorganism such as an alga, a nucleic acid construct such as a vector, a plasmid, a nucleic acid backbone with or without control sequence (e.g., promoter, etc.) or other nucleic acid molecule with or without a coding sequence. The nucleic acid construct can be codon optimized for use with the organism. The kits further can include instructions for performing any method or part of a method described herein. The kits can include a transducer or part of a transducer.

EXAMPLES

Having generally described embodiments drawn to methods of ultrasound mediated delivery of substances to cells or organisms using bubbles, a further understanding can be obtained by reference to certain specific examples which are provided herein for purposes of illustration only, and are not intended to be limiting.

Example 1

Microbubble Stock Preparation

Microbubble stock preparation was prepared according to the following protocol:
1. In 10 mLs of PBS mix 200 mg 1,2-dipalmitoyl-sn-glycero-3-phosphatidylcholine and 50 mg 1,2-dipalmitoyl-sn-glycero-3-phosphatidylethanolamine with 1 g glucose.
2. Heat the mixture in boiling water bath 20-30 minutes, pipette mixing every 5 minutes.
3. The solution can be stored at 4° C. for up to 6 months.

Example 2

Microbubble/Nucleic Acid Preparation

A microbubble/nucleic acid preparation was prepared according to the following protocol:

1. Take a 250 μL of the prepared microbubble stock solution from Example 1 above and incubate at 40° C. for 15 minutes.
2. The pre-warmed microbubble solution is then transferred to a 1.5 mL microtube containing 50 μL of glycerol.
3. 1-2 mg of purified plasmid DNA encoding an expression construct for the gene of interest (purified in this example by Qiagen Endotoxin free MegaPrep kit, Qiagen, Germantown, Md., with an optimal concentration of 4 mg/mL). 2.4) Phosphate-buffered saline is added to a final volume of 500 μL. Endotoxin free Qiagen maxipreps are used, as well as sterile PBS in order to ensure sterility.
4. The air in the microtube is then replaced with Octafluoropropane gas.
5. The microtube is then shaken vigorously in a dental amalgamator for 20 seconds.
6. The subnatant containing residual DNA and buffer that has not bound to the microbubbles is then carefully removed and the microbubble layer is washed three times with sterile PBS to remove unattached DNA, and placed on ice between each wash cycle. All reagents are sterile and care is made to minimize contamination. In some embodiments, a binding efficiency of 30-40% can result.
7. The plasmid DNA-bound microbubbles are then placed on ice for up to two hours until use.
8. The subnatant removed from the microtube after mixing and the PBS washes, can be used to determine the concentration of unbound DNA, and likewise the amount bound based upon the known initial concentration, by measuring the optical density of this solution at a wavelength of 260 nm using a spectrophotometer.

Example 3

Ultrasound Targeted Microbubble Destruction (UTMD)

Ultrasound targeted microbubble destruction (UTMD) mediated transfection of algae was performed in vitro using the following protocol:
1. UTMD mediated transfection was performed using an Olympus 0.5" unfocused immersion transducer with a working frequency of 1.0 Mhz.
2. $1 \times 10^7$ cells were suspended in 1 mL PBS in a 24-well plate. 50-200 ul of microbubble stock solutions was added to suspension.
3. Transducer was immersed. Cell volume: $1 \times 10^7$ cells/1 mL PBS.
4. Transducer staged 1 cm into 24 well plate
5. A 380 mVpp waveform pulsed through a fixed 55 dB gain power amplifier producing a continuous waveform (sinewave in this case) for 10 seconds (a 40 W output) was applied to the cells.
6. Cells were replaced in media and allowed to grow for 2 days before evaluation.

Parameter variance that produced effects included:
200 kHz-1.1 MHz frequency range
0.8-200 W power range
0.1-4.0 mechanical index
In some embodiments, waveform may not matter, if it is continuous or arbitrary.

Example 4

Transformation of C. reinhardtii with GFP and CFP Constructs

*Chlamydomonas reinhardtii*, a species of unicellular green algae, has been particularly well researched; the genome of *C. reinhardtii* has been fully sequenced, it has been genetically engineered to produce recombinant proteins and growth kinetics have been recorded and improved through various means [4], [5]. Additionally, a basic qualitative understanding of the organelles which make up *C. reinhardtii* has been previously researched [6]. However, a more detailed quantitative and dynamic understanding of the anatomy may aid in the optimization of recombinant protein production and isolation and may also give insight into algal growth and maturation patterns.

One approach that can be used to better understand the anatomy and function of algae, such as *C. reinhardtii*, is protein localization. Protein localization techniques typically take advantage of short amino acid sequences which act like postal codes; the cell recognizes these specific sequences and the protein is shuttled to the associated organelle. See for example, Nelson et al., "A multicolored set of in vivo organelle markers for co-localization studies in *Arabidopsis* and other plants," *The Plant journal for cell and molecular biology*, 51(6):1126-1136 (2007), which is incorporated herein by reference in its entirety, including all targeting sequences and nucleic acid constructs and sequences, methods and techniques described therein. For example, a specific signal sequence at the N-terminus of a protein may direct this product to the secretory pathway, while a different sequence at the C-terminus may retain the protein in the endoplasmic reticulum. These sequences may consist of less than 5 amino acids but may also range above hundreds of amino acids in length. See id. Typically, a long targeting sequence is undesirable for shorter proteins as it may interfere with the integrity and function of the protein. See id.

Wild type *C. reinhardtii* cells of strain mt-[137c], obtained from the *Chlamydomonas* Research Center (St. Paul, Minn.), were grown at room conditions on a shaker at 120 rpm at a light intensity of 120 μE/(m$^2$s) to a cell density of approximately 10$^6$ cells/mL as determined by a cell count using a hemocytometer. 1 mL of cells were transferred to a single well of a 12 well microtiter plate (Sigma-Aldrich, Oakville, Ontario) and the UTMD technique described above in Example 3 was used to transiently transform the cells, following the standard transformation procedure. See also Walton et al. ("Introduction to the ultrasound targeted microbubble destruction technique," Journal of visualized experiments: JoVE 52 (2011), which is incorporated herein by reference in its entirety, including without limitation for its methods, materials, devices and techniques). Several different DNA constructs were purified and used for separate transformations of algae. In total, 7 constructs cloned into *E. coli* were obtained from the *Arabidopsis* Biological Research Center (Ohio State University), while an additional 3 constructs were prepared by the inventors. A combination of bacterial selection methods (kanamycin or ampicillin) and fluorescent protein colors were used to allow flexible combinations of constructs. Refer to Table 1 below for a detailed list of all constructs transformed into *C. reinhardtii*.

TABLE 1

| Targeted Organelle | Plasmid No. | Color of Fluorescent Protein | Arabidopsis Stock No. | Bacterial Stock Resistance |
|---|---|---|---|---|
| Untargeted | 673 | Green | N/A | Ampicillin |
| Actin | 822 | Green | N/A | Ampicillin |
| Endoplasmic Reticulum | 823 | Cyan | CD3-953 | Kanamycin |
| Golgi body | 824 | Cyan | CD3-961 | Kanamycin |
| Mitochondria | 825 | Cyan | CD3-985 | Kanamycin |
| Peroxisome | 826 | Cyan | CD3-977 | Kanamycin |
| Plastid | 827 | Cyan | CD3-993 | Kanamycin |
| Plasma Membrane | 828 | Cyan | CD3-1001 | Kanamycin |
| Vacuole | 829 | Cyan | CD3-969 | Kanamycin |
| Secretory Pathway | 850 | Green | N/A | Ampicillin |

*E. coli* cells were grown on the appropriate selective media and DNA vectors were purified from the bacterial cells using E.Z.N.A. Plasmid Miniprep Kits (Omega Bio-tek Inc., Norcross, Ga.). Following transformation, the algae cells were left to recover in the dark for 48 hours with no agitation at room conditions. Sterile techniques were used to diminish the likelihood of contamination.

Following the recovery period of 48 hours, 20 µL of the transformed cell culture of interest was prepared onto a microscope slide for cellular imaging using confocal microscopy.

An Olympus Fluoview FV10i (Olympus Canada Inc., Richmond Hill, Ontario) laser scanning confocal microscope was used to observe and capture images of the transgenic cells. All images were captured using an Olympus UPlanSApo 60× oil immersion objective (Olympus Canada Inc., Richmond Hill, Ontario). An additional digital magnification of 3× (total magnification of 180×) was applied using the Fluoview FV10i 1.2a software. Laser excitation and emission wavelengths for green fluorescent protein were set to 489 nm and 510 nm, respectively, while cyan fluorescent protein excitation and emission wavelengths were set to 428 nm and 536 nm, respectively. Where applicable, chlorophyll autofluorescence was imaged using an excitation wavelength of 473 nm and an emission wavelength of 670 nm Following image capture, images were cropped and scale bars were added using Olympus cellSens software.

Results

Figure 3:
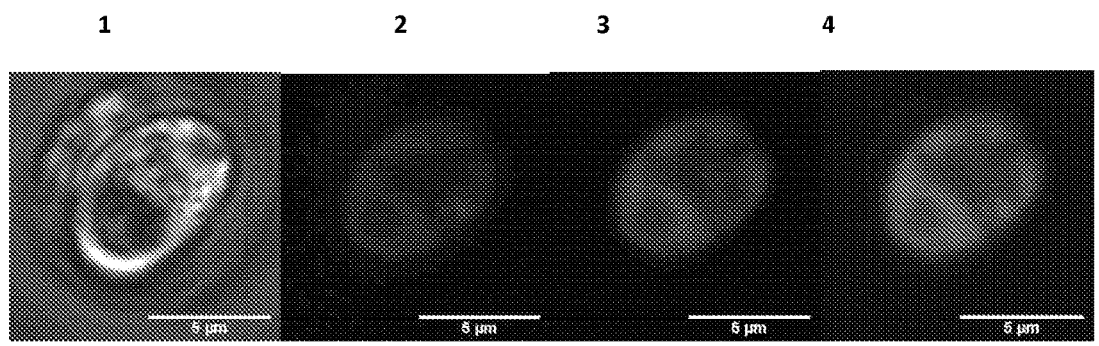
FIG. 3: Wild type *Chlamydomonas reinhardtii* cells observed under a laser scanning confocal microscope. Column 1 shows phase contrast, 2 is GFP fluorescence, 3 is chlorophyll autofluorescence and 4 is a merge of 2 and 3. A large amount of chlorophyll autofluorescent is observed in panel 3, outlining the "U" shaped chloroplast. Apart from autofluorescence, note the lack of fluorescence in panel 2. All images were captured at a total magnification of 180×, and a scale bar is shown for each image.
Figure 4:
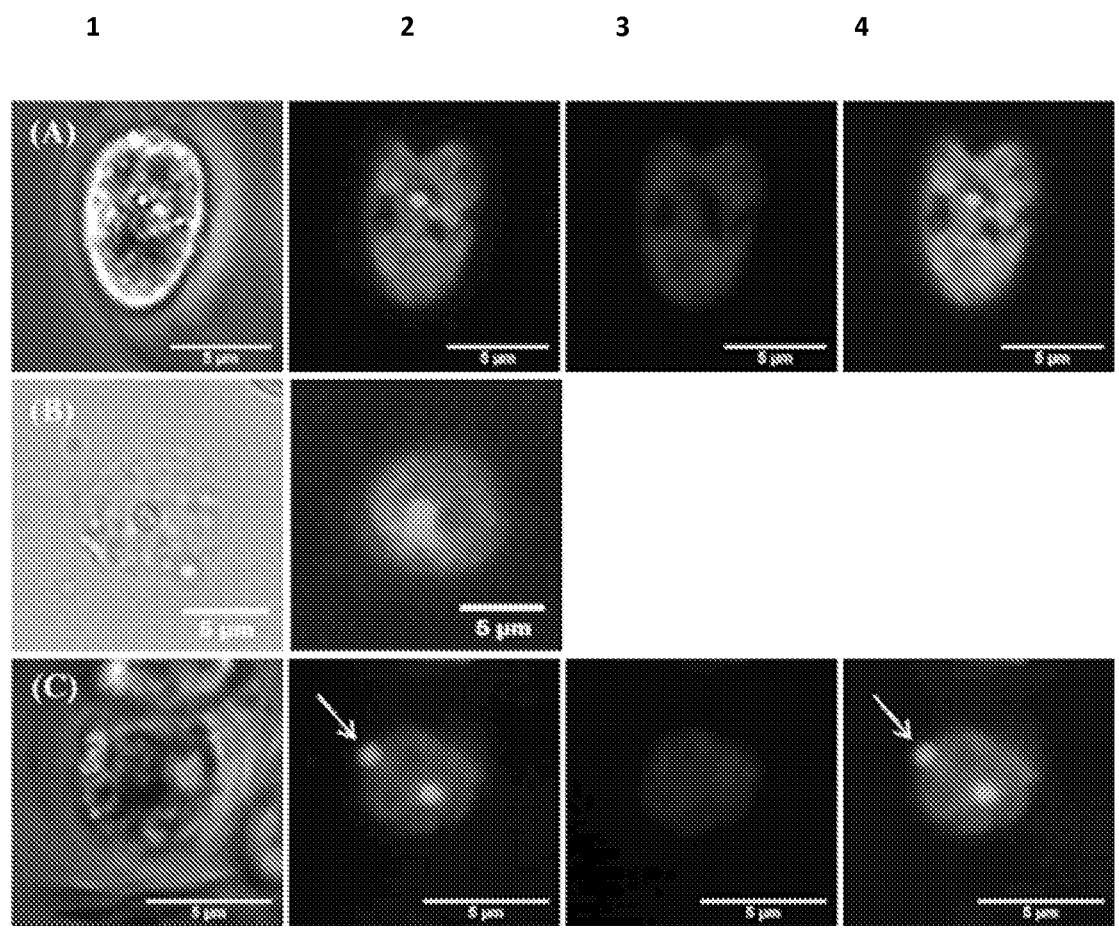
FIG. 4: *Chlamydomonas reinhardtii* transformed with various DNA constructs coding for green fluorescent protein (GFP) targeted to different organelles. Column 1 shows phase contrast images, 2 shows GFP emission, 3 shows chlorophyll autofluorescence and 4 is a merge of 2 and 3. Non-targeted GFP. Note GFP fluorescence in the cytoplasm and the chloroplast. Actin-targeted GFP. A network of fluorescence was observed throughout the entire cell. Chlorophyll autofluorescence is not shown for this construct. GFP targeted to the secretory pathway. The arrows indicate GFP sequestered to a vesicle near the edge of the plasma membrane. All images were captured at a total magnification of 180× using a laser scanning confocal microscope, and a scale bar is shown for each image.

In total, 10 different organelles were targeted for localization of fluorescent proteins. For comparative purposes, FIG. 3 shows wild type *C. reinhardtii* which underwent the UTMD transformation technique in the absence of exogenous DNA. FIGS. 4 and 5 display the GFP and CFP constructs, respectively. Each fluorescently tagged organelle showed distinct characteristics when observed under a fluorescent microscope.

Discussion of Results of UTMD w/Out Exogenous Nucleic Acid

FIG. 3 shows a laser scanning confocal microscope image of a wild type (mt-[137c]) *Chlamydomonas reinhardtii* cell which had undergone the UTMD procedure without the addition of exogenous DNA. A large amount of chlorophyll autofluorescence was observed, as seen in the third panel, which is typical of green alga cells. The outline of the "U" shaped chloroplast can be clearly identified, and the circular shape of the chloroplastic pyrenoid can be distinguished in the bottom of the "U". The GFP emission filter also collected some of this autofluorescent background signal, as seen in the second panel. However, when a merge of both the autofluorescence and GFP channels is displayed in the fourth panel, the red autofluorescence almost entirely cancels out the green GFP signal. This merged image showed only a very minute amount of residual GFP signal, which is typical of noise or debris commonly observed in wild type cells. This wild type control allowed for a comparison to any putitive transgenic cell; large signals of CFP or GFP observed in merged images, apart from autofluorescence, can be attributed to the transgenic cell.

Discussion of Results of UTMD w/GFP Construct

FIG. 4(A) shows the results from the other control used in this experiment—a construct which did not selectively target GFP to any cellular organelle. In this case, the DNA construct did not include coding for a targeting peptide sequence. As such, GFP was observed throughout the cytoplasm and the chloroplast of the entire cell. This result is peculiar because it was hypothesized that GFP would only be present in the cytoplasm of the cell. There should be no way for the fluorescent protein to pass the membrane-bound chloroplast because there was no targeting sequence on the GFP and molecular chloroplastic chaperones will not transport the fluorescent protein. Therefore, it is hypothesized that the UTMD transformation technique successfully introduced the exogenous plasmid DNA to both the cytoplasm and the chloroplast. The chloroplast, having the proper machinery to express exogenous DNA, could then transiently produce GFP. This hypothesis, if correct, could potentially show that the UTMD technique could be used to insert exogenous DNA into the nucleus for stable homologous recombination with the nuclear genome. If the energy of the DNA is great enough to penetrate the cell wall, the plasma membrane and the chloroplastic membrane, it is possible that the DNA could penetrate the nuclear membrane. This hypothesis is an area of future research.

GFP targeted to cellular actin is shown in FIG. 4 (B). Although an autofluorescent image was not available, a network of fluorescence was observed throughout the cell. The cytoskeleton, which is partially comprised of actin filaments, is highlighted in panel 2 of FIG. 4(B).

FIG. 4(C) displays GFP targeted to the secretory pathway of the algae cell. Although it was hypothesized that secreted vesicles or small collections of GFP would be observed in the extracellular matrix, this was not seen experimentally. However, FIG. 4(C) captures a fluorescent image which appears to show a vesicle of GFP on the edge of the plasma membrane (as seen in the white arrow), perhaps in preparation for secretion by exocytosis. It is hypothesized that exocytosis of the vesicle's contents would quickly dilute the GFP into the extracellular matrix, making it unobservable.

Discussion of Results of UTMD w/CFP Construct

Figure 5A:
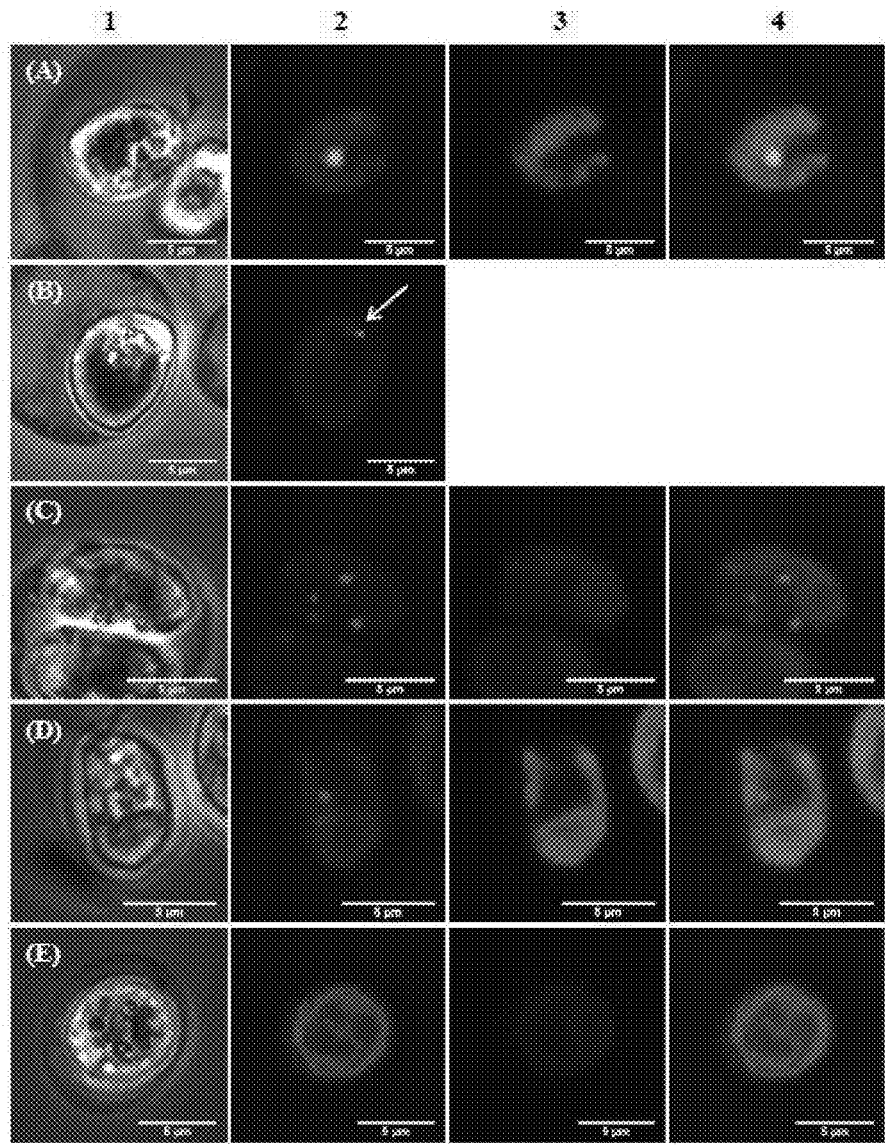
FIG. 5A and FIG. 5B: *Chlamydomonas reinhardtii* transformed with various DNA constructs coding for cyan fluorescent protein (CFP) targeted to different organelles. Column 1 shows phase contrast images, 2 shows CFP fluorescence emission, 3 shows chlorophyll autofluorescence and 4 is a merge of 2 and 3. (A) CFP targeted to the endoplasmic reticulum (Note a high level of fluorescence around the nucleus of the cell). (B) CFP targeted to the Golgi body. A long, thin signal is shown near the terminal end of the cell. Chlorophyll autofluorescence is not shown for this construct. (C) Mitochondrion-targeted CFP. Four separate fluorescent signals are observed both near to and away from the chloroplast. (D) Peroxisome-targeted CFP. A small amount of fluorescence is observed in one area. (E) CFP targeted to the plastid (chloroplast). Strong fluorescence is observed primarily throughout the chloroplastic region. (F) CFP targeted to the cellular membrane. Fluorescence is observed along the outside of the cell. Chlorophyll autofluorescence is not shown for this construct. (G) Vacuole-targeted CFP. Two separate fluorescent signals are localized within the cell. All images were captured at a total magnification of 180× using a laser scanning confocal microscope, and a scale bar is shown for each image.

The 8 CFP constructs used were previously expressed in *A. thaliana*. In this study, these constructs have been shown to be expressed in the green alga *Chlamydomonas reinhardtii*. FIG. 5A in the panels of row (A) shows localization of CFP to the endoplasmic reticulum. A strong fluorescence signal was observed near the nucleus of the cell, as hypothesized. Although it was also thought that a network surrounding the nucleus would be observed, this was not seen experimentally. Instead, a fluorescent signal extended slightly from the nucleus before diminishing.

FIG. 5A in the panels of row (B) displays CFP targeted to the Golgi body. A long, thin fluorescent signal was observed in the upper region of the cell. In comparison to FIG. 6(B), which shows an electron micrograph of *C. reinhardtii*, the experimentally tagged Golgi body was located in a similar cellular region between the nucleus and the chloroplast, and also had a similar size and shape.

The fluorescent signal from four mitochondria is seen in FIG. 5A in the panels of row (C). As FIG. 6(C) shows, several mitochondria are dispersed throughout a typical *C. reinhardtii* cell. These organelles are present in relatively low numbers during phototrophic growth, but several more may be observed when cells are grown in heterotrophic culture conditions.

A small fluorescent signal from a single peroxisome was observed as seen in FIG. 5A in the panels of row (D). These small organelles are typically found in low copy numbers within the cell.

Figure 6:
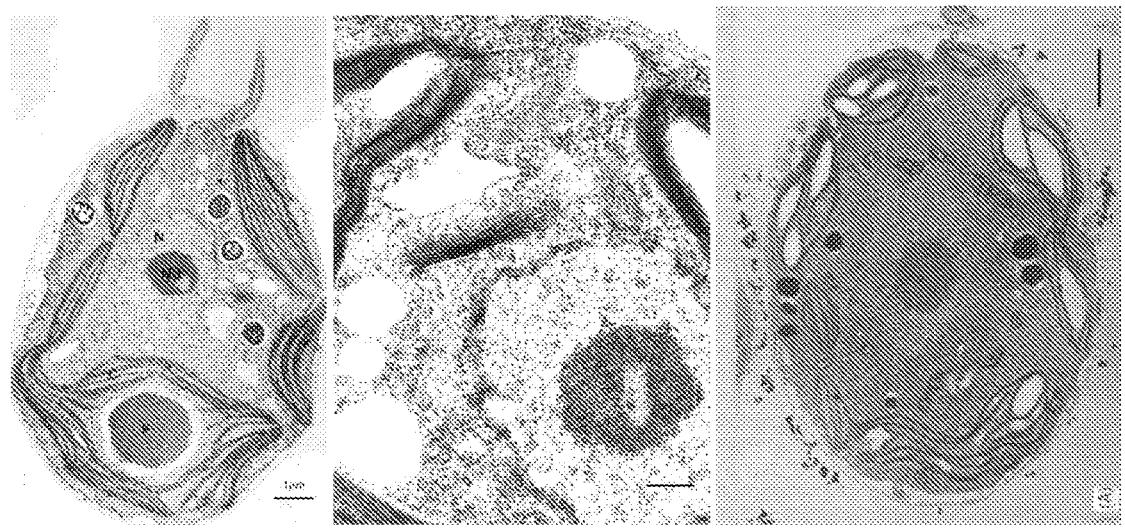
FIG. 6: Electron micrographs of wild type *Chlamydomonas reinhardtii*. Visible organelles are the nucleus (N), the nucleolus (Nu), the chloroplast (C), the pyrenoid (P), the Golgi body (G), vacuole (V) and mitochondria (M). The scale bar for images (A) (image on left) and (C) (image on the right) is 1 μm, while the scale bar for image (B) (image on the right) is 0.5 μm.

FIG. 5A in the panels of row (E) displays CFP targeted to the chloroplastic region of the cell. A strong signal was observed throughout the chloroplast. All panels in FIG. 6 show the theoretical position of the chloroplast within the cell. For anatomical purposes this DNA construct is moot due to red chlorophyll autofluorescence; however, it may still be desirable to target recombinant proteins to the chloroplastic region of the cell. Transgenic proteins often accumulate to much higher levels in the chloroplast as compared to expression in the nuclear genome, primarily because the chloroplastic genome lacks gene silencing mechanisms found frequently in the nuclear genome. Furthermore, proteins targeted to the chloroplast or produced in the chloroplast are not glycosylated, which may be essential for the production of recombinant proteins such as certain antibodies or vaccines which must maintain a specific, non-glycosylated organization in order to be functional.

Figure 5B:
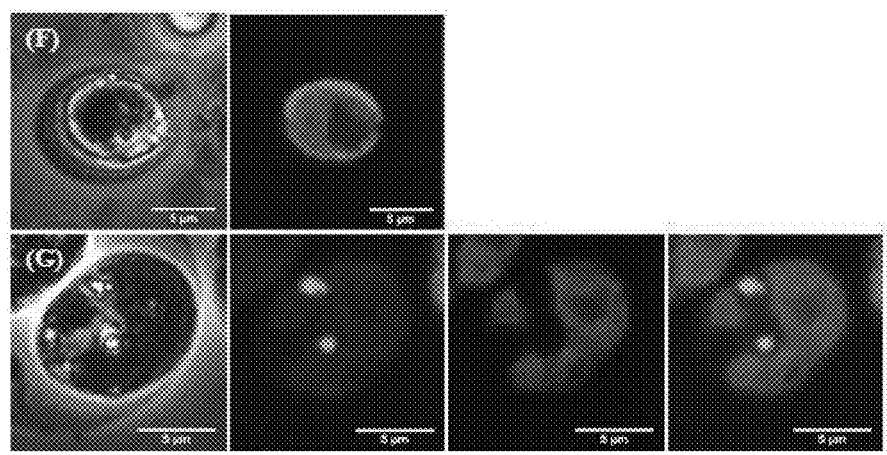

Fluorescence from CFP targeted to the plasma membrane is shown in FIG. 5B in the panels of row (F). The single layer plasma membrane surrounds the cytoplasm on all sides, allowing for the observed distribution of cyan fluorescent protein along the entire outer edge of the cell.

Finally, FIG. 5B in the panels of row (G) displays CFP targeted to cellular vacuoles. Unlike plant cells which often have a single large vacuole, algae cells have several smaller vacuoles distributed throughout the cell, as seen in FIG. 6 (B).

Summary and Conclusions

In summary, ultrasound mediated delivery (e.g., UTMD) can be utilized for the delivery of targeted fluorescent proteins to cellular organelles, which can give detailed insight into the anatomy of cells. In some embodiments, several different colors of fluorescent proteins can be combined to show many organelles or structures at one time.

Furthermore, those of skill in the art can utilize the exogenous molecule delivery methods described herein, for example, to produce medically relevant recombinant proteins such as vaccines or biopharmaceuticals in host organisms such as algae. Certain organelles or pathways, such as the chloroplast or the secretory pathway as described above, may have superior traits which may be exploited for benefits in protein production or separation. These characteristics may significantly increase total protein production, or may reduce the cost and complexity of separation.

The embodiments illustrated in this Example, and the other embodiments described herein illustrate the use of ultrasound mediated delivery of substances to algae, such as for example, nucleic acid molecules and proteins, to name a few. Some embodiments relate to delivery of such substances in a targeted manner, and the use of ultrasound actually many unexpectedly improve such targeted delivery due to effects of the ultrasound and/or the cavitation on intracellular organelles, membranes and barriers. Genetically engineered unicellular algae are a potentially inexpensive and efficient source of complex recombinant proteins. Some embodiments herein relate to methods for delivering or facilitating the delivery of substances to algae, including to specific organelles, structures or locations within the algae and analyzing the anatomy, physiology, anatomy, etc. of the algae that comprise the delivered substance, for example to identify pathways and structures. Detailed information into the anatomy and physiology of the algal cell may give insight into previously unknown pathways or structures. Furthermore, this information can be used to identify an optimal area for the production or sequestration of recombinant proteins, for example, by showing areas of high activity, etc.

This Example highlights many different cellular structures using organelle-targeted fluorescent proteins. *C. reinhardtii* cells were transiently transformed with various DNA constructs using the UTMD transformation technique. Cells were imaged under a laser scanning confocal microscope at a total magnification of 180×. Fluorescent images of organelles in transgenic cells were compared to the theoretical position of organelles in electron micrographs, confirming the successful targeting of fluorescent proteins.

Example 5

UTMD Transformation of *Chlamydomonas* with a GUS Reporter

Figure 7:
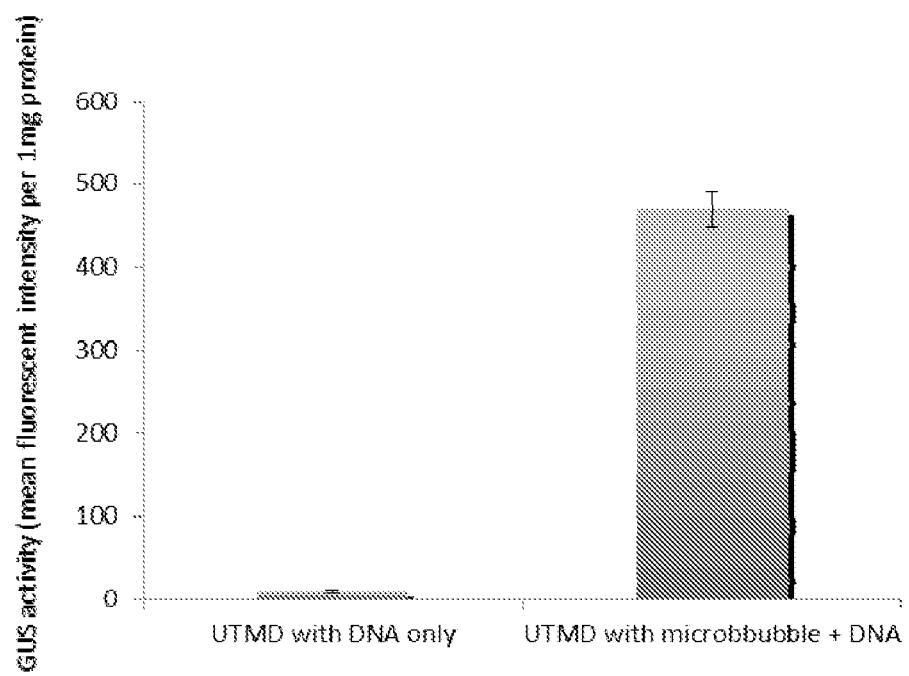
FIG. 7: *Chlamydomonas* sp. was transformed with a CaMV driven GUS reporter construct. After 24 hours of post-treatment incubation, the algae were processed and reporter GUS activity was measured using fluorometry.

*Chlamydomonas* sp. was transformed with a CaMV driven GUS reporter construct using UTMD with a 15 second pulse of a 1.1 MHz transducer at a MI of 1.7, and 100 μl of microbubble solution (~40 μg DNA) in a 5 ml culture (~1 mg protein content per 1 ml). After 24 hours of post-treatment incubation, the algae were processed and reporter GUS activity was measured using fluorometry (FIG. 7).

Example 6

UTMD Transformation of *Nannochloropsis oceanica* with a GUS Reporter

*Nannochloropsis oceanica* was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes and then again after 60 minutes. See Table 2.

TABLE 2

GUS activity (mean fluorescent intensity per 1 mg protein, minus background and negative control)

| | $A^1$ | $B^1$ | $A^2$ |
|---|---|---|---|
| *Nannochloropsis oceanica* | 6.841 | 0 | 55.122 |
| *Micromonas* sp. | 3.125 | UT | UT |
| *Tetraselmis* sp. | 3.604 | UT | UT |
| *Chlamydomonas* sp. | 0 | 0.77 | 21.313 |
| *Staurosira* sp. | 0 | 0 | UT |
| *Entomoneis* sp. | 3.511 | 2.345 | 0 |

UT: Untested

A: UTMD Treatment protocol=Function generated; 1 MHz sinewave, 1 Vpp, +55 dB (MI=1.3); Transducer=0.5 MHz, 0.25" diameter, and Culture conditions; 1 ml algae ($10^6$ cells) and 40 ug plasmid.

B: UTMD Treatment protocol=1 MHz sinewave, 1 Vpp, +55 dB (MI=1.3; Transducer=1 MHz 0.5" diameter, and Culture conditions; 5 ml algae ($10^6$ cells) and 40 ug plasmid.
[1]20 minute GUS kinetic assay
[2]60 minute GUS kinetic assay
Cells exposed to UTMD for 10 second pulse with microbubbles coated with CaMV driven β-glucuronidase. GUS assay performed 24 hours post-UTMD treatment.

Example 7

UTMD Transformation of *Micromonas* with a GUS Reporter

*Micromonas* sp. was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes. See Table 2.

Example 8

UTMD Transformation of *Tetraselmis* sp. with a GUS Reporter

*Tetraselmis* sp. was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes. See Table 2.

Example 9

UTMD Transformation of *Chlamydomonas* sp with a GUS Reporter

*Chlamydomonas* sp. was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes and then again after 60 minutes. See Table 2.

Example 10

UTMD Transformation of *Staurosira* Sp with a GUS Reporter

*Staurosira* sp. was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes. See Table 2.

Example 11

UTMD Transformation of *Entomoneis* Sp with a GUS Reporter

*Entomoneis* sp. was transformed with a CaMV driven GUS reporter construct using UTMD with a 10 second pulse of a 1.1 MHz transducer at a MI of 1.3, and 100 μl of microbubble solution (~40 μg DNA) in a 5 mL culture. After 24 hours of post-treatment incubation, the algae were processed (~1 mg protein content per 1 ml) and reporter GUS activity was measured using fluorometry. GUS activity was measured after 20 minutes. See Table 2.

Example 12

UTMD Transformation of *Chlamydomonas* with a GFP Reporter

Figure 8:
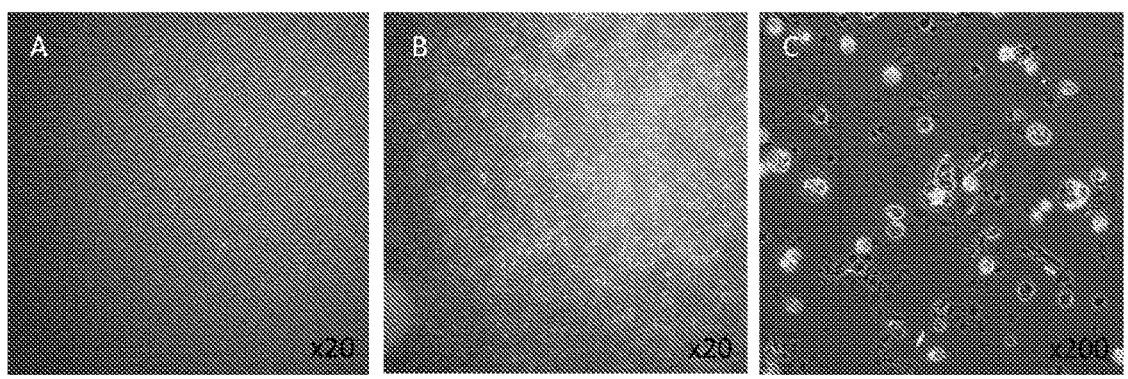
FIG. 8: UTMD Transformation of *Chlamydomonas* with a GFP Reporter.

*Chlamydomonas* sp. was transformed with a CaMV driven GFP reporter construct using UTMD with a 10 second pulse of a 1.1 MHz transducer at a MI of 1.7, and 100 μl of microbubble solution (~40 μg DNA) in a 5 ml culture ($10^6$ cells/mL). After 48 hours of post-treatment incubation, the algae were imaged for GFP fluorescence (FIG. 8. A. UTMD with no microbubbles (plasmid DNA only), B. UTMD with microbubbles+plasmid DNA, and C. Light field and GFP merge of UTMD with microbubbles+plasmid DNA). Transformation efficiency was assessed by counting 9 random field of views from 3 separate experiments (×100 magnified images of bright field and GFP merge images were used), for a total of 27 views, for GFP positive versus GFP negative cells. Result: 78%+/−8% (A 70-85% efficiency in transformation was achieved with this method).

Example 13

UTMD Transformation of *Chlamydomonas* with a GFP Reporter

Figure 9:
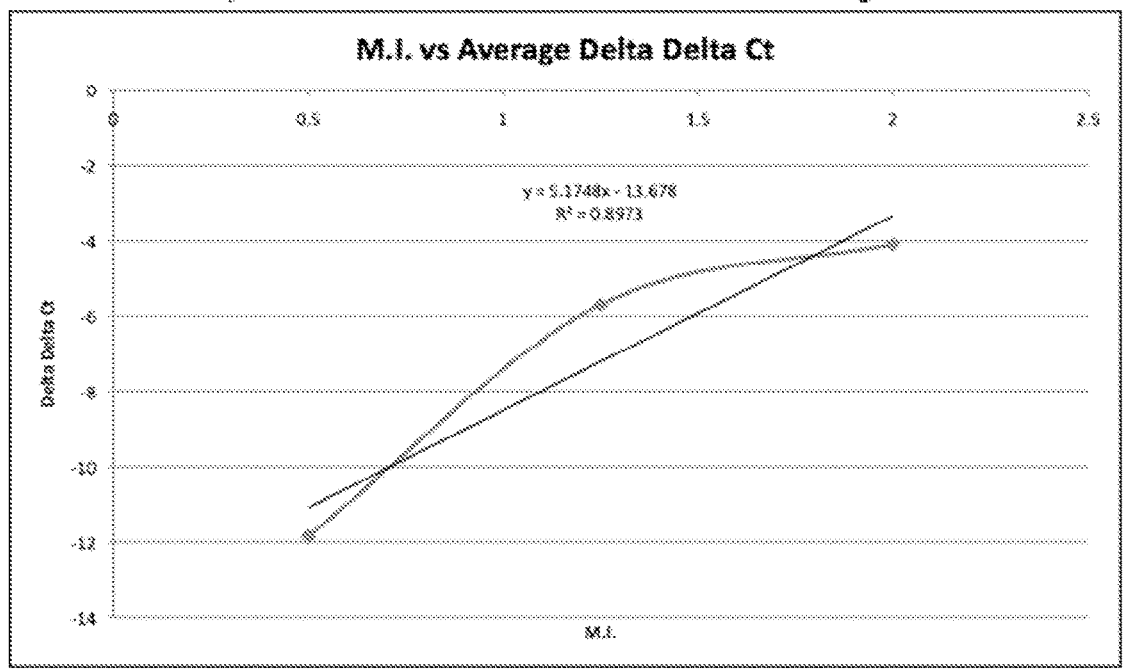
FIG. 9: qPCR validation results of UTMD Transformation of *Chlamydomonas* with a GFP Reporter.

*Chlamydomonas* sp. was transformed with a CaMV driven GFP reporter construct using UTMD with a 10 second pulse of a 1.1 MHz transducer at a MI of 0.5, 1.1, and 2.0, and 100 μl of microbubble solution (~40 μg DNA) in a 5 ml culture ($10^6$ cells/mL). After 48 hours of post-treatment incubation, the algae were processed and qPCR was conducted on isolated RNA and qPCR normalized (using the Delta/Delta Ct method) to; algae subjected to UTMD without microbubbles (using GFP primers), and 18S RNA ("housekeeping" gene primers) (FIG. 9).

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes both the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein. The word "exemplary" is used exclusively herein to mean "serving as an example, instance, or illustration." Any implementation described herein as "exemplary" is not necessarily to be construed as preferred or advantageous over other implementations. Additionally, a person having ordinary skill in the art will readily appreciate, the terms "upper" and "lower" are sometimes used for ease of describing the figures, and indicate relative positions corresponding to the orientation of the figure on a properly oriented page, and may not reflect the proper orientation of the device as implemented.

Certain features that are described in this specification in the context of separate implementations also can be implemented in combination in a single implementation. Conversely, various features that are described in the context of a single implementation also can be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

The term "plurality" refers to two or more of an item. The term "about" means quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide. Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "about 1 to 5" should be interpreted to include not only the explicitly recited values of about 1 to about 5, but also include individual values and sub-ranges within the indicated range. Thus, included in this numerical range are individual values such as 2, 3 and 4 and sub-ranges such as 1-3, 2-4 and 3-5, etc. This same principle applies to ranges reciting only one numerical value (e.g., "greater than about 1") and should apply regardless of the breadth of the range or the characteristics being described. A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

While the above description has pointed out novel features of the invention as applied to various embodiments, the skilled person will understand that various omissions, substitutions, and changes in the form and details of the device or process illustrated may be made without departing from the scope of the invention. Therefore, the scope of the invention is defined by the claims that follow rather than by the foregoing description. All variations coming within the meaning and range of equivalency of the claims are embraced within their scope.

What is claimed is:

1. A method of introducing an exogenous material into an algae, comprising:
providing an algae;
providing a population of bubbles that comprise one or more nucleic acid molecules and/or one or more polypeptide or protein molecules;
contacting the population of bubbles with the algae;
subsequently applying ultrasound to the bubbles and algae with sufficient energy to cavitate one or more of bubbles comprising the one or more nucleic acid molecules in proximity to the algae; and
maintaining the algae and the one or more burst bubbles comprising the one or more nucleic acid molecules in contact for a period of time sufficient to permit entry of at least one nucleic acid molecule into the algae.

2. The method of claim 1, wherein the algae is unicellular.

3. The method of claim 1, wherein the algae is a unicellular green algae, a unicellular red algae, a unicellular yellow-green algae, a unicellular brown algae, a unicellular blue-green algae, a unicellular diatom, a unicellular haptophyte, a unicellular dinoflagellate, a unicellular cyanobacterium, or a unicellular eustigmatophyte.

4. The method of any of claim 1, wherein the algae is not prokaryotic.

5. The method of claim 1, wherein the algae is a microalgae.

6. The method of claim 1, wherein the algae is selected from the group consisting of *Nannochloropsis* sp., *Micromonas* sp., *Tetraselmis* sp., *Chlamydomonas* sp., *Staurosira* sp., *Entomoneis* sp. and *Dunaliella* sp.

7. The method of claim 1, wherein the algae is present at a concentration of $10^2$-$10^{12}$ cells per 1 mL of culture.

8. The method of claim 1, wherein the bubbles are microbubbles.

9. The method of claim 8, wherein the microbubbles comprise a substance comprising one or more of a lipid, a protein, a surfactant, a polyelectrolyte multilayer shell, and a polymer.

10. The method of claim 9, wherein the substance comprises one or more of 1,2-dipalmitoyl-sn-glycero-3-phosphatidylcholine and 1,2-dipalmitoyl-sn-glycero-3-phosphatidylethanolamine, SPAN-10/TWEEN-40, albumin, alginate, poly(D,L-lactide-co-glycolide) (PLGA)), poly(vinyl alcohol) (PVA), and polyperfluorooctyloxycaronyl-poly (lactic acid) (PLA-PFO).

11. The method of claim 1, wherein the bubbles have diameter of about 0.2 μM-5 μM.

12. The method of claim 1, wherein the one or more nucleic acid molecule comprises a miRNA, shRNA, siRNA, circular nucleic acid construct, plasmid DNA, a transposase construct, or a viral nucleic acid construct.

13. The method of claim 1, wherein the one or more nucleic acid molecule comprises a sequence encoding a protein, a polypeptide or a peptide.

14. The method of claim 1, wherein the protein, a polypeptide or a peptide is an antibody, an antibody fragment, an enzyme, a cytokine, a chemokine, an antigen, a neurotrophin, a hormone, a brain derived neurotrophic factor, a fluorescent protein, an interleukin, a growth factor, a toxin, a signal sequence, a transcription factor, a report molecule, a promoter, or a polypeptide or protein comprising a coding sequence and/or non-coding that is at least partially optimized for algal expression.

15. The method of claim 1, wherein the one or more nucleic acid molecules and/or one or more polypeptide and/or protein molecules are coated onto the bubbles.

16. The method of claim 1, wherein the one or more nucleic acid molecules and/or one or more polypeptide and/or protein molecules are bound or attached to the bubbles.

17. The method of claim 16, wherein the one or more nucleic acid molecules and/or one or more polypeptide and/or protein molecules are bound or attached to the bubbles via an electrostatic or ionic bond, or via conjugation.

18. The method of claim 1, wherein the one or more nucleic acid molecules and/or the one or more polypeptide and/or protein molecules are coated onto the bubbles at a concentration of 1 mg nucleic acid per 1 mL final volume microbubble solution.

19. The method of claim 1, wherein the applying ultrasound to the bubbles and algae comprises applying ultrasound at a center frequency range of about 0.2 KHz to about 3 MHz.

20. The method of claim 1, wherein the ultrasound is applied at a Mechanical Index (MI) of between about 0.1 to 4.0.

21. The method of claim 1, wherein the ultrasound is applied at a power range of between about 0.5 and 200 W power range.

22. A method of transforming an algae, comprising contacting microalgae at a concentration of between $1 \times 10^6$ cells to about $1 \times 10^8$ cells per 1 mL of a solution with microbubbles comprising one or more nucleic acid molecules at a concentration of 1-1000 μg per 1 mL of algal solution; applying ultrasound to the contacted microalgae and microbubbles for a period ranging from about 5 seconds to 20 seconds by at least partially submerging an ultrasound transducer into the solution, wherein the ultrasound has one or more of a frequency of 0.2 KHz to 2.0 MHz, a mechanical index (MI) of 0.1 to 4.0, a power range of 0.5 to 200 W; and wherein the applying of ultrasound is sufficient to break or burst one or more microbubbles such that the one or more nucleic acid molecules can enter into one or more of the microalgae.

23. The method of claim 22, wherein the microbubbles comprise a material at least partially having a positive charge sufficient to create an electrostatic attraction with the one or more nucleic acid molecules.

* * * * *